United States Patent
Reinhard

(10) Patent No.: US 8,048,078 B2
(45) Date of Patent: Nov. 1, 2011

(54) TOOL FOR MAKING DRILL-HOLES IN BONES OR REMOVING CYLINDRICAL DRILL-HOLE CORES FROM BONES OF THE HUMAN BODY

(75) Inventor: Helmut Reinhard, Frankfurt (DE)

(73) Assignee: Reinhard Feinmechanik GmbH, Dietzenbach (DE)

( * ) Notice: Subject to any disclaimer, the term of this patent is extended or adjusted under 35 U.S.C. 154(b) by 943 days.

(21) Appl. No.: 12/006,586

(22) Filed: Jan. 3, 2008

(65) Prior Publication Data
US 2008/0167652 A1 Jul. 10, 2008

(30) Foreign Application Priority Data
Jan. 9, 2007 (DE) .................. 10 2007 002 089

(51) Int. Cl.
*A61B 17/16* (2006.01)
(52) U.S. Cl. .......................................... 606/80; 279/24
(58) Field of Classification Search ............ 606/79, 606/80, 81, 82, 99; 623/20.35; 408/147; 279/2.22, 19.5, 24, 79, 104, 23.1, 46.1, 76; 403/109.1, 109.2, 116, 329, 379.5, 326, 366, 403/367; 285/360; *A61B 17/16*
See application file for complete search history.

(56) References Cited

U.S. PATENT DOCUMENTS

| | | | | |
|---|---|---|---|---|
| 1,205,280 A | * | 11/1916 | Sommer | 403/379.5 |
| 2,037,307 A | * | 4/1936 | Bowman | 175/419 |
| 7,175,643 B2 | | 2/2007 | Shi | |
| 2007/0123891 A1 | | 5/2007 | Ries et al. | |

FOREIGN PATENT DOCUMENTS

| | | |
|---|---|---|
| DE | 85 13 328.0 | 10/1985 |
| DE | 198 03 998 A1 | 2/1998 |
| DE | 103 57 104 A1 | 7/2005 |
| EP | 1 447 194 A1 | 8/2004 |
| GB | 2 310 623 A | 9/1997 |
| JP | 04105811 | 4/1992 |
| JP | 09117814 | 5/1997 |
| WO | WO 99/38450 | 8/1999 |

\* cited by examiner

*Primary Examiner* — Thomas C. Barrett
*Assistant Examiner* — Christian Sevilla
(74) *Attorney, Agent, or Firm* — Reising Ethington P.C.

(57) ABSTRACT

A tool (1) is constructed for single use for making drill-holes in bones or removing cylindrical drill-hole cores from bones of the human body with a tubular tool body (2) which can be inserted into a receiving bore (8) of a tool holder (4). At least one cutout (5) in the tool body (2) and at least one protrusion (10) of the tool holder are coupled to rotationally affix the tool (1) to the tool holder (4). In the process, a flexible tongue (15) on the tool body (2) latches into an opening (16) of the tool holder (4) to axially fix the tool body. After the tool (1) has been used, the tongue (15) can be pushed out of the opening from outside, with plastic deformation, so that the tool can no longer be connected to the tool holder (4).

13 Claims, 2 Drawing Sheets

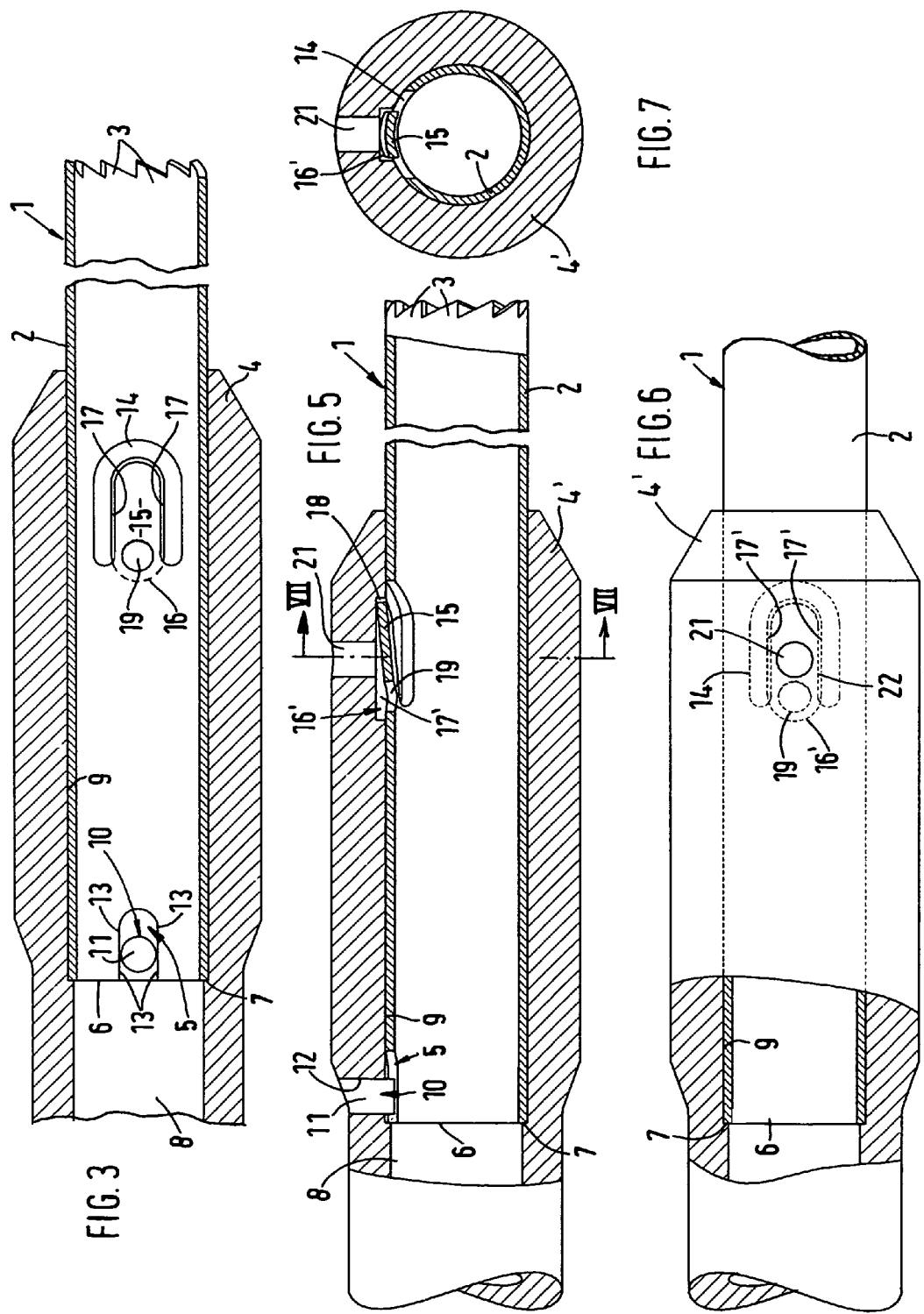

TOOL FOR MAKING DRILL-HOLES IN BONES OR REMOVING CYLINDRICAL DRILL-HOLE CORES FROM BONES OF THE HUMAN BODY

TECHNICAL FIELD

The invention relates to a tool for making drill-holes in bones or removing cylindrical drill-hole cores from bones of the human body.

PRIOR ART

In reconstructive surgery, tools which are driven in rotation and which have a cutting and/or grinding action are used to make drill-holes in bones and to obtain cylindrical drill-hole cores from bones. For the operator, it is not always possible in an unambiguous manner to assess the cutting or grinding elements of the tools with regard to a sufficient cutting or grinding performance. Therefore, in order to achieve a sufficient cutting or grinding performance, the tools should be used just once. However, the known tool designs can be connected to and detached from the tool holder of the drive device as often as desired, so that one-off use is not guaranteed.

PROBLEM

What is needed is a tool which is designed as a tool for single use and which, with low production costs and a low installation space requirement, can be securely connected just once to the drive device.

SUMMARY OF THE INVENTION

A tool according to the invention is characterized in that the tool body has at its inner end a cutout which extends as far as the end face of the tool body, in which cutout a protrusion which protrudes from the inner wall surface of the tool holder is received when the tool body is inserted into the tool holder as far as a stop, and in that an outwardly projecting tongue which is cut out of the wall of the tool body and points towards the outer end of the tool body is provided at an axial distance from the cutout, which tongue, when the tool body is pushed into the tool holder and immediately before the tool body reaches the stop, enters an assigned opening in the wall of the tool holder, in a manner such as to prevent any axial displacements of the tool body in the tool holder, from which opening it can be bent out only with permanent deformation of the tongue in order to remove the tool body from the tool holder.

On the tool according to the invention, those elements which produce the rotationally fixed connection between the tool body and the tool holder, namely the cutout in the tool body and the protrusion of the tool holder, are arranged respectively on the tool body and tool holder in such a way as to be functionally and spatially separate from those elements which produce the one-off axial fixing of the tool body in the tool holder, namely the flexible tongue of the tool body and the opening assigned thereto in the wall of the tool holder. When the tool body is inserted into the tool holder as far as the stop, it is connected in a rotationally fixed manner to the tool holder and is driven in rotation by the latter when the drive device is actuated accordingly. Due to the engagement of the tongue in the assigned opening in the wall of the tool holder, the tool body cannot be axially pulled out of the tool holder and the tool is ready for use. This axial locking can be released only by exerting pressure on the tongue from outside, whereby the tongue is plastically deformed in such a way that it cannot spring back into the opening in the wall of the tool holder. With the tool thus made unusable, the tool body can be pulled out of the tool holder and reinserted, but it can no longer be fixed axially in the tool holder due to the fact that the tongue has become unusable. During the insertion of the tool body into the tool holder, the tongue that has been pushed outward during manufacture of the tool is bent back into the wall of the tool body in a partially elastic and partially plastic manner, so that the tool body can be inserted into its tool holder, whereby the tongue elastically springs into the opening in the tool holder when it reaches this opening.

Advantageously, in a continuation of the concept of the invention, the arrangement is such that the tongue has a reduced cross-sectional area in the region of its tongue root due to the provision of a hole through the tongue wall. Depending on the size and geometric shape of this opening, just two narrow webs from the wall of the already thin-walled tubular tool body remain on either side of the hole as far as the tongue edge, so that the tongue, prior to removal of the tool from the tool holder, can easily be bent out of the opening in the tool holder from outside and moved permanently into the interior of the tubular tool body. Any residual elasticity of the tongue still remaining at the start of the bending-out process is quickly converted into a plastic deformation, i.e. permanent deformation, so that the tool thus made unusable can be pulled out of its tool holder and discarded. Given a suitable choice of material for the tool body, which is preferably made of a corrosion-resistant austenitic or martensitic steel, and given a suitable size and shape of the hole in the tongue root and a sufficiently large bending-out travel, the tongue may even break in the region of the two thin webs during the bending-out process, which is especially desirable in the context of the tool then being unusable.

Advantageously, the protrusion protruding from the inner wall surface of the tool holder is part of a round bolt fixed radially in a bore of the tool holder, while the cutout in the tool body which receives the protrusion is U-shaped with two wall surfaces parallel to one another and to the longitudinal axis of the tool body. The round bolt can be inseparably connected to the tool holder by welding or soldering. Its round cross-sectional shape facilitates the pushing-on of the U-shaped cutout of the tool body when inserting the tool body into the tool holder.

The opening in the wall of the tool holder which is assigned to the tongue may be designed as an elongate hole with two wall surfaces parallel to one another and to the longitudinal axis of the tool holder. In this case, the full length and width of the tongue is visible from outside through the opening, so that the tongue is exposed for engagement of a tool during the bending-out process.

In a preferred variant, the opening in the wall of the tool holder which is assigned to the tongue is designed as an inner groove section with two wall surfaces parallel to one another and to the longitudinal axis of the tool holder, wherein the inner groove section is connected to the outer surface of the tool holder only via a radially arranged access bore. This variant offers two significant advantages over the arrangement described above. On the one hand, with regard to the desired creation of a tool for single use, any manipulation of the tongue by the user is ruled out by the narrow cross section of the access bore. On the other hand, a small leakage amount of water which flows as cooling fluid through the tool body flows off to the side due to the relatively small cross section of the access bore and the associated higher flow resistance.

Preferably, the cutout in the tool body with the associated protrusion of the tool holder on the one hand and the tongue of the tool body with the associated opening in the wall of the tool holder on the other hand are arranged one behind the other and aligned with one another in the axial direction. However, the tool may also be designed such that the cutout in the tool body with the associated protrusion of the tool holder, relative to the tongue of the tool body with the associated opening in the wall of the tool holder, are arranged rotated through an angle with respect to one another about the common longitudinal axis of the tool body and tool holder. In this case, any angle which does not hinder or which even improves the handling of the tool can be selected, so long as it is ensured that it is of equal size for the tool body and for the tool holder.

The dimensioning of the engaging parts of the tool body and tool holder in the circumferential direction should advantageously be such that, when the protrusion of the tool holder bears against the relevant wall surface of the cutout in the tool body, there is a gap between the tongue and the wall surface of the elongate hole or inner groove section located closest to it in the driven rotation direction. This ensures that the torque exerted by the tool holder on the tool body is transferred onto the tool body only by the protrusion and not by the tongue.

BRIEF DESCRIPTION OF THE DRAWINGS

The invention will be explained in greater detail below in an example of embodiment with reference to the drawings which are enlarged relative to the actual dimensions and are partially schematic. In the drawings:

FIG. 3 shows the sectional view along the section line III-III in FIG. 1, FIG. 5 shows a longitudinal section similar to FIG. 1, but with a variant of the opening in the wall of the tool holder which is designed as an inner groove section and receives the tongue, FIG. 6 shows the arrangement shown in FIG. 5, in a partially broken-open plan view, and FIG. 7 shows the cross-sectional view along the section line VII-VII in FIG. 5.

DETAILED DESCRIPTION OF THE EXAMPLE OF EMBODIMENT

Figure 1:
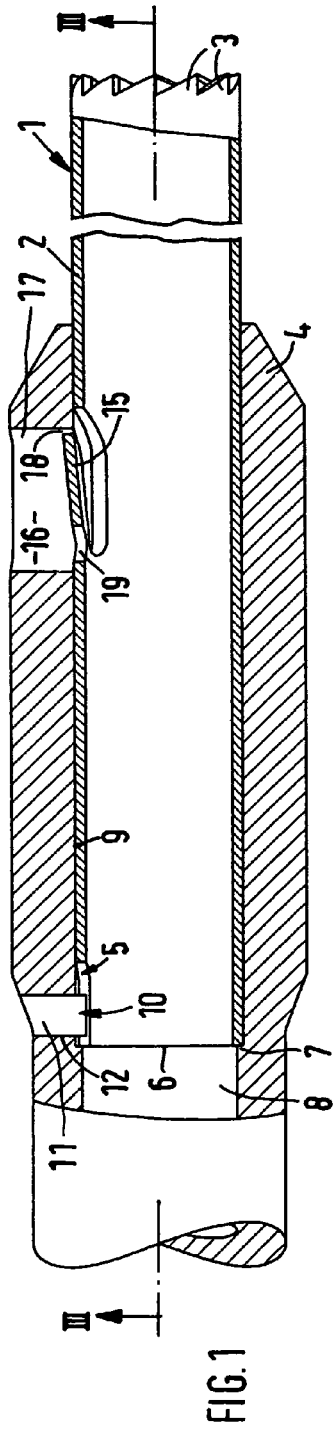
FIG. 1 shows, substantially in longitudinal section, a tool inserted into a tool holder in a manner ready for use, with an opening in the wall of the tool holder which is designed as an elongate hole and receives the tongue.

Reference is firstly made to FIGS. 1 to 4. As can be seen therefrom, the tool generally denoted by reference numeral 1 consists of a thin-walled tubular tool body 2 made of steel, which is provided with cutting or grinding elements 3 at its outer end. In the example shown, these are teeth-like cutting elements. The tool body 2 is inserted axially into a likewise tubular tool holder 4, which tightly surrounds the tool body 2 but allows displacement movements of the tool body 2 during insertion into the tool holder and removal from the tool holder. The tool holder 4, which is shown broken off at its inner end, can be connected to a drive device (not shown) for driving the tool holder 4 and thus the tool 1 in rotation.

Provided at the inner end of the tool body 2 is a cutout 5 which passes through the wall thickness of the tool body 2 and extends as far as the end face 6 of the tool body 2, i.e. is open towards this side. When the tool body is fully inserted, this end face 6 bears against a stop 7 designed as an annular step in the cylindrical receiving bore 8 of the tool holder 4, in such a way as to limit the travel.

A protrusion 10 protrudes from the inner wall surface 9 of the tool holder 4 into the receiving bore 8, which protrusion is received by the cutout 5 when the tool body 2 is inserted into the tool holder 4 as far as the stop 7. The protrusion 10 protruding from the inner wall surface 9 of the tool holder 4 is part of a round bolt 11 which is fixed in a bore 12 of the tool holder 4. The cutout 5 in the tool body 2 which receives the protrusion 10 is U-shaped, as can be seen from FIGS. 3 and 4, and has two wall surfaces 13 parallel to one another and to the longitudinal axis of the tool body 2.

Figure 4:
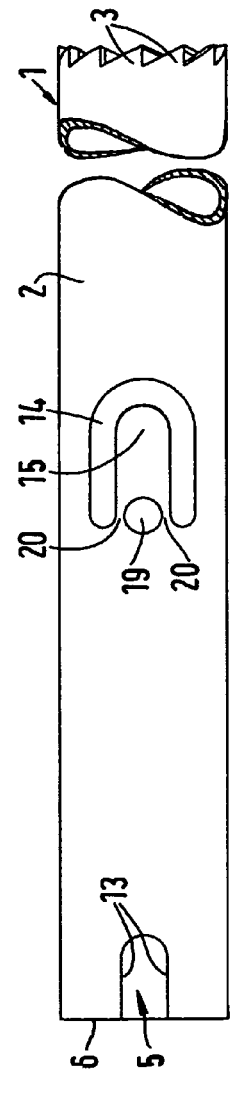
FIG. 4 shows the plan view of the tool.

As can best be seen from FIG. 4, a tongue 15 formed from the wall of the tool body 2 by a U-shaped free cut 14 is provided at an axial distance from the cutout 5, which tongue is arranged pointing towards the outer end of the tool body 2 and projects outwards under plastic deformation of the material, as can be seen from FIG. 1. Opposite the tongue 15 there is an opening 16 in the wall of the tool holder 4 which is assigned to the tongue. This opening 16 passing through the wall thickness is designed as an elongate hole with two wall surfaces 17 parallel to one another and to the longitudinal axis of the tool holder 4. The width of the opening 16, i.e. the distance between the wall surfaces 17, is larger than the width of the tongue 15.

Figure 2:
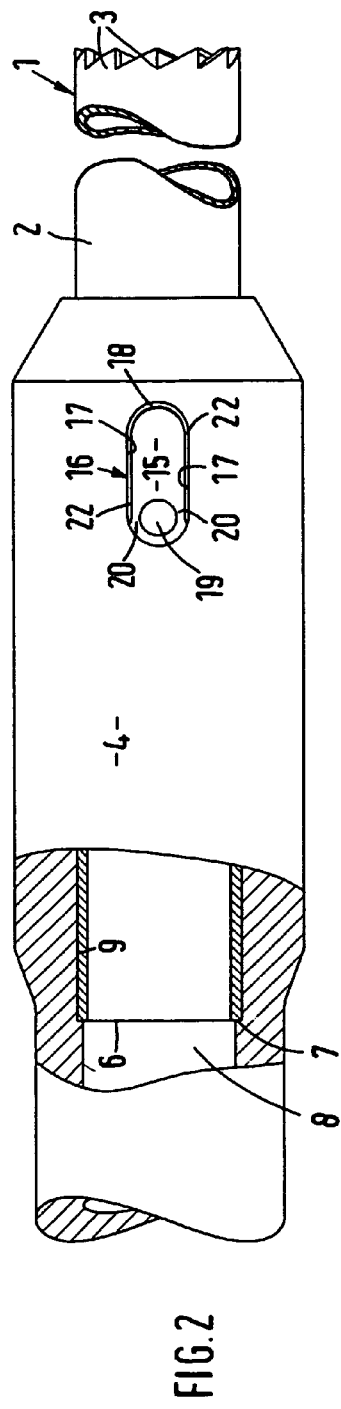
FIG. 2 shows the arrangement shown in FIG. 1, in a partially broken-open plan view.

When the tool body 2 is inserted into the receiving bore 8 of the tool holder 4, the tongue 15, which in the process is bent back into the wall of the tool body 2, enters the opening 16 assigned to it in the wall of the tool holder 4 immediately before the end face 6 of the tool body 2 reaches the stop 7, as a result of which the tool body 2 is locked in the tool holder 4 in such a way that it cannot be pulled out of the tool holder 4. When the end face 6 bears against the stop 7, as shown in FIG. 1, there is a narrow gap 18 between the front free tongue end and the adjacent rounded wall section of the opening 16 (FIG. 2).

When the tool 1 is to be removed from the tool holder 4 after use, an object suitable for pushing down on the tongue 15 is inserted into the opening 16 from outside, by means of which the tongue 15 is bent downwards out of the opening 16 into the interior of the tool body 2, wherein the plastic deformation which occurs in the process in the region of the tongue root is great enough that, at the end of the force exertion on the tongue 15, the latter can no longer enter the opening 16 for locking purposes. The tool 1 for single use can then be pulled out of the tool holder 4 and is made unusable for further drilling uses.

In order to facilitate the bending-out process, the tongue 15 has a reduced cross-sectional area in the region of its tongue root due to the provision of a hole 19 through the tongue wall, so that only two narrow webs 20 which can easily be deformed are left between the hole 19 and the tongue edge.

The variant shown in FIGS. 5 to 7 of the example of embodiment described up to now with reference to FIGS. 1 to 4 differs only with regard to the locking engagement of the tongue 15 with the tool holder. In this case, the opening 16' in the wall of the tool holder 4' which is assigned to the tongue 15 does not pass through the entire wall thickness but rather forms only an inwardly open inner groove section with two wall surfaces 17' parallel to one another and to the longitudinal axis of the tool holder 4'. This opening 16' designed as an inner groove section is connected to the outer surface of the tool holder 4' only via a radially arranged access bore 21. This relatively narrow access bore 21 prevents undesirable manipulations on the tongue 15 once bent out of the opening 16' and only allows the tongue 15 to be bent out of the opening 16' by means of a pin-shaped object which fits into the access bore 21.

In the described example of embodiment with its two variants with regard to the tongue engagement with the tool holder 4 or 4' in a locking manner in the axial direction, the cutout 5 in the tool body 2 with the associated protrusion 10 of the tool holder 4, 4' on the one hand and the tongue 15 of the tool body 2 with the associated opening 16 or 16' in the wall of the tool holder 4, 4' on the other hand are arranged one behind the other and aligned with one another in the axial direction. However, as already mentioned above, the arrangement may also be such that the cutout 5 with the protrusion 10 on the one hand, relative to the tongue 15 with the associated opening 16, 16' on the other hand, are arranged rotated through an angle with respect to one another about the common longitudinal axis of the tool body 2 and tool holder 4, 4'.

When the protrusion 10 of the tool holder 4 bears against the relevant wall surface 13 of the cutout 5 in the tool body 2 as shown in FIG. 3, there is a gap 22 between the tongue 15 and the wall surface 17 of the opening 16 located closest to it in the driven rotation direction. This gap 22 prevents any bearing of the edge of the tongue 15 against a wall surface 17, so as to prevent the tool 1 from also being driven in rotation via the tongue 15.

There is proposed a tool intended for single use for making drill-holes in bones or removing cylindrical drill-hole cores from bones of the human body. The tool has a tubular tool body which can be inserted into a receiving bore of a tool holder, wherein at least one cutout in the tool body and at least one protrusion of the tool holder enter into coupling engagement in order to connect the tool in a rotationally fixed manner to the tool holder. In the process, a tongue provided in a flexible manner on the tool body latches into an opening of the tool holder in order to axially fix the tool body. After the tool has been used, the tongue can be irreversibly pushed out of the opening from outside, with plastic deformation, so that the tool can no longer be connected to the tool holder.

Other variations and modifications are possible without departing from the scope and spirit of the present invention as defined by the appended claims.

LIST OF REFERENCES 1 tool
2 tool body
3 cutting or grinding elements
4, 4' tool holder
5 cutout
6 end face
7 stop
8 receiving bore
9 inner wall surface
10 protrusion
11 round bolt
12 bore
13 wall surfaces
14 free cut
15 tongue
16, 16' opening
17, 17' wall surfaces
18 gap
19 hole
20 webs
21 access bore
22 gap

The invention claimed is:

1. A tool for making drill-holes in bones or removing cylindrical drill-hole cores from bones of the human body, including a tubular tool body which can be driven in rotation about its longitudinal axis, which tool body can be connected in a rotationally fixed and axially non-displaceable manner to a tool holder of the drive device which tightly surrounds it, and is provided with cutting or grinding elements at its outer end, said tool characterized in that the tool body has at its inner end a cutout which extends as far as an end face of the tool body;

a protrusion which protrudes radially inward from an inner wall surface of the tool holder and is received in the cutout when the tool body is inserted into the tool holder as far as a stop;

an outwardly projecting tongue integrally formed with the wall of the tool body and points towards the outer end of the tool body is provided at an axial distance from the cutout; the tongue, when the tool body is pushed into the tool holder and immediately before the tool body reaches the stop, enters an opening in the wall of the tool holder, in a manner such as to prevent any axial displacements of the tool body in the tool holder, from which opening it can be bent out only with permanent deformation of the tongue in order to remove the tool body from the tool holder; and the tongue has a reduced cross-sectional area in the region of its tongue root due to the provision of a hole through the tongue and said permanent deformation occurs at said reduced cross-sectional area.

2. A tool according to claim 1 further characterized by:
the protrusion protruding from the inner wall surface of the tool holder is part of a round bolt fixed radially in a bore of the tool holder, and the cutout in the tool body which receives the protrusion is U-shaped with two wall surfaces parallel to one another and to the longitudinal axis of the tool body.

3. A tool according to claim 1 further characterized by:
the opening in the wall of the tool holder which is assigned to the tongue is designed as an elongate hole with two wall surfaces parallel to one another and to the longitudinal axis of the tool holder.

4. A tool according to claim 1 further characterized by:
the opening in the wall of the tool holder which is assigned to the tongue is designed as an inner groove section with two wall surfaces parallel to one another and to the longitudinal axis of the tool holder, wherein the opening designed as an inner groove section is connected to the outer surface of the tool holder only via a radially arranged access bore.

5. A tool according to claim 1 further characterized by:
the cutout in the tool body with the associated protrusion of the tool holder on the one hand and the tongue of the tool body with the associated opening in the wall of the tool holder on the other hand are arranged one behind the other and aligned with one another in the axial direction.

6. A tool according to claim 1 further characterized by:
the cutout in the tool body with the associated protrusion of the tool holder, relative to the tongue of the tool body with the associated opening in the wall of the tool holder, are arranged rotated through an angle with respect to one another about the common longitudinal axis of the tool body and tool holder.

7. A tool according to claim 1 further characterized by:
when the protrusion of the tool holder bears against the relevant wall surface of the cutout in the tool body, there is a gap between the tongue and the wall surface of the opening located closest to it in the driven rotation direction.

8. A tool for use with bone of the human body, including a tubular tool body which can be driven in rotation about its longitudinal axis, which tool body can be connected in a rotationally fixed and axially non-displaceable manner to a tool holder of the drive device which tightly surrounds it, and is provided with cutting or grinding elements at its outer end, said tool characterized by:
the tool body having one of a groove and protrusion and said tool holder having the other groove and protrusion;
said groove and protrusion engage each other when the tool body is inserted into the tool holder to prevent relative rotation of the tool holder with respect to the tool body;
an outwardly projecting tongue which is cut out of the wall of the tool body and points towards the outer end of the tool body is provided at an axial distance from the one of the groove and protrusion; and
the tongue, when the tool body is pushed into the tool holder and immediately before the tool body reaches a stop enters an opening in the wall of the tool holder, in a manner such as to prevent any axial displacements of the tool body in the tool holder, from which opening it can be bent out only with permanent deformation of the tongue in order to remove the tool body from the tool holder; and the tongue has a reduced cross-sectional area in the region of its tongue root due to the provision of a hole through the tongue and said permanent deformation occurs at said reduced cross-sectional area.

9. A tool according to claim 8 further characterized by:
the opening in the wall of the tool holder which is assigned to the tongue is designed as an elongate hole with two wall surfaces parallel to one another and to the longitudinal axis of the tool holder.

10. A tool according to claim 8 further characterized by:
the opening in the wall of the tool holder which is assigned to the tongue is designed as an inner groove section with two wall surfaces parallel to one another and to the longitudinal axis of the tool holder, wherein the opening designed as an inner groove section is connected to the outer surface of the tool holder only via a radially arranged access bore.

11. A tool for use with bones of the human body, including a tubular tool body which can be driven in rotation about its longitudinal axis, which tool body can be connected in a rotationally fixed and axially non-displaceable manner to a tool holder of the drive device which tightly surrounds it, and is provided with cutting or grinding elements at its outer end, said tool characterized by:
the tubular tool body has an integrally formed outwardly projecting tongue which is cut out of the wall of the tool body and points towards the outer end of the tubular tool body;
the tongue, when the tubular tool body is pushed into the tool holder and immediately before the tubular tool body reaches a stop enters an opening in the wall of the tool holder, in a manner such as to prevent any axial displacement of the tool body in the tool holder, from which opening it can be bent out only with permanent deformation of the tongue in order to remove the tool body from the tool holder; and
the tongue has a reduced cross-sectional area in the region of its tongue root due to the provision of a hole through the tongue and said permanent deformation occurs at said reduced cross-sectional area.

12. A tool according to claim 11 further characterized by:
the opening in the wall of the tool holder which is assigned to the tongue is designed as an elongate hole with two wall surfaces parallel to one another and to the longitudinal axis of the tool holder.

13. A tool according to claim 11 further characterized by:
the opening in the wall of the tool holder which is assigned to the tongue is designed as an inner groove section with two wall surfaces parallel to one another and to the longitudinal axis of the tool holder, wherein the opening designed as an inner groove section is connected to the outer surface of the tool holder only via a radially arranged access bore.

* * * * *